(12) United States Patent
Teague

(10) Patent No.: US 8,734,465 B2
(45) Date of Patent: *May 27, 2014

(54) STONE RETRIEVAL DEVICE AND RELATED METHODS OF MANUFACTURE

(75) Inventor: James A. Teague, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/400,769

(22) Filed: Feb. 21, 2012

(65) Prior Publication Data

US 2012/0209282 A1 Aug. 16, 2012

Related U.S. Application Data

(63) Continuation of application No. 11/122,324, filed on May 5, 2005, now Pat. No. 8,142,445.

(60) Provisional application No. 60/568,268, filed on May 6, 2004.

(51) Int. Cl.
*A61B 17/22* (2006.01)

(52) U.S. Cl.
USPC .......................................... 606/127; 606/113

(58) Field of Classification Search
USPC ..................... 606/127, 113, 114, 46, 47, 200; 604/523–527
See application file for complete search history.

(56) References Cited

U.S. PATENT DOCUMENTS

| | | | |
|---|---|---|---|
| 3,108,593 A * | 10/1963 | Glassman ..................... | 606/127 |
| 4,790,812 A | 12/1988 | Hawkins, Jr. et al. | |
| 4,846,392 A | 7/1989 | Hinshaw | |
| 5,443,472 A * | 8/1995 | Li ................................. | 606/114 |
| 5,741,429 A | 4/1998 | Donadio, III et al. | |
| 6,099,537 A | 8/2000 | Sugai et al. | |
| 6,419,679 B1 | 7/2002 | Dhindsa | |
| 6,458,145 B1 | 10/2002 | Ravenscroft et al. | |
| 6,500,182 B2 * | 12/2002 | Foster ......................... | 606/127 |
| 6,921,397 B2 | 7/2005 | Corcoran et al. | |
| 7,316,692 B2 * | 1/2008 | Huffmaster ................... | 606/127 |
| 7,970,347 B2 * | 6/2011 | Hart et al. .................... | 455/13.1 |
| 2002/0026203 A1 * | 2/2002 | Bates et al. .................. | 606/127 |
| 2002/0068943 A1 | 6/2002 | Chu et al. | |
| 2002/0068954 A1 | 6/2002 | Foster | |
| 2004/0026942 A1 | 2/2004 | Kessler et al. | |
| 2004/0054377 A1 | 3/2004 | Foster et al. | |

FOREIGN PATENT DOCUMENTS

DE 197 22 429 A1 12/1998

OTHER PUBLICATIONS

Written Opinion of the International Searching Authority issued in International Application No. PCT/US2005/015729, dated Oct. 26, 2005.
International Search Report issued in International Application No. PCT/US2005/015729, dated Oct. 26, 2005.
Official Communication Pursuant to Article 94(3) EPC mailed Mar. 18, 2008 in European Patent Application No. 05 742 340.2.

* cited by examiner

*Primary Examiner* — Tuan V Nguyen
(74) *Attorney, Agent, or Firm* — Bookoff McAndrews, PLLC

(57) ABSTRACT

A medical device includes an elongate member having a plurality of flexibility features and a basket having a plurality of legs. The elongate member and the basket are formed from a single piece of a material. The flexibility features are formed by removing first portions of the material to increase flexibility of the elongate member. The legs are formed by removing longitudinal portions of the material.

18 Claims, 6 Drawing Sheets

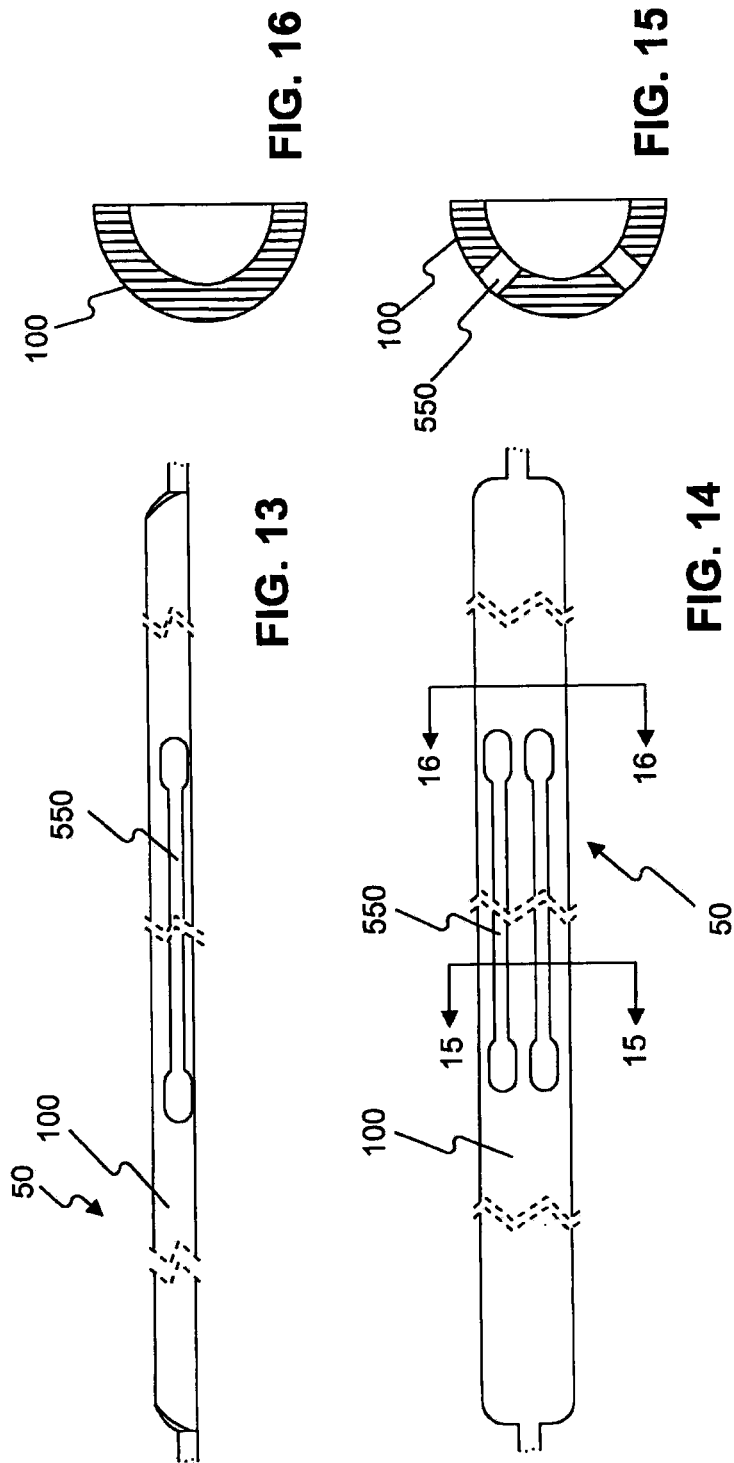

STONE RETRIEVAL DEVICE AND RELATED METHODS OF MANUFACTURE

PRIORITY DATA

This application is a continuation of U.S. patent application Ser. No. 11/122,324, filed May 5, 2005, now U.S. Pat. No. 8,142,445, which claims the benefit of U.S. Provisional Application No. 60/568,268, filed May 6, 2004, all of which are incorporated by reference in their entirety.

FIELD OF THE INVENTION

This disclosure relates generally to a medical device and more particularly to stone retrieval devices and methods of manufacturing the same.

BACKGROUND OF THE INVENTION

Extractors have been used for the removal of stones or calculi from within the body. One type of extractor has a sheath and includes a basket at its distal end. The basket may be collapsed within the sheath to achieve a reduced diameter profile. The basket may also be opened when it extends beyond the sheath. Once opened, a targeted stone may be captured within the basket.

The baskets of some extractors include wires that are joined via soldering or welding to form a ball or nub. Manufacturing such devices can be costly and time consuming. The baskets of other extractors have wires that are twisted or knotted together to eliminate a soldered or welded tip at the distal end. The tips of these devices, however, may hinder access to stones or calculi, and may increase the possibility of tissue damage.

The present disclosure provides stone retrieval devices and methods of manufacturing the same that avoid some or all of the aforementioned shortcomings of existing devices.

SUMMARY OF THE INVENTION

In an exemplary embodiment of the present disclosure, a medical device includes an elongate member having a plurality of flexibility features and a basket having a plurality of legs. The elongate member and the basket are formed from a single piece of a material. The flexibility features are formed by removing first portions of the material to increase flexibility of the elongate member. The legs are formed by removing longitudinal portions of the material.

In embodiments, the single piece of the material is one of a rod, a tube, a cannula, and a stent. The elongate member may be substantially hollow and at least one of the plurality of flexibility features may extend through only a part of a wall of the elongate member. The elongate member may comprise a metal coated with a polymer. In addition, the flexibility features may be disposed along at least one of a proximal portion and a distal portion of the elongate member. At least one of the plurality of flexibility features may extend completely through a wall of the elongate member and the single piece of the material may be one of a flat sheet and a partial cylinder. At least two of the plurality of flexibility features may define interlocking shapes. In addition, the flexibility features may be oriented around at least part of a circumference of the elongate member.

In exemplary embodiments, a distal end of the basket may be one of blunt, rounded, and tipless. At least two legs of the plurality of legs may have the same length and width and the basket may further include retrieval material disposed between at least a portion of at least two legs of the plurality of legs. The retrieval material may extend along an entire length of at least one of the at least two legs. At least one leg of the plurality of legs may be coated with a protection material. Moreover, the basket may be disposed proximal a distal portion of the elongate member.

In another exemplary embodiment of the present disclosure, a method of manufacturing a medical device includes removing longitudinal portions of a first section of a single piece of material to form a plurality of legs of a basket and removing second portions of a second section of the single piece of material to form a plurality of flexibility features of an elongate member. The first and second sections being different sections of the single piece of material.

In embodiments, removing longitudinal portions of the first section includes one of laser cutting, chemical etching, die cutting, and mechanically slicing. In addition, removing second portions of the second section may include one of laser cutting, chemical etching, die cutting, and mechanically slicing. Removing second portions of the second section may also include forming interlocking neighboring portions of the elongate member. Removing second portions of the second section could further include removing an entire portion of a wall of the single piece of material.

Embodiments also include attaching retrieval material to at least two legs of the plurality of legs. Attaching retrieval material may include one of welding, grafting, and tying. Methods may further include coating at least one leg of the plurality of legs with a protection material and folding the single piece of material at the plurality of legs to form a portion of the basket.

In a further exemplary embodiment of the present disclosure, a method of manufacturing a medical device includes removing longitudinal portions of a section of a single piece of a partial cylinder to form a plurality of legs. The method also includes folding the single piece of a partial cylinder at the section to form a basket and attaching a proximal end of the folded single piece of to an actuating member.

In embodiments, the single piece of the partial cylinder is approximately one half of one of a cannula, a stent, and a hollow tube. Methods may further include forming a plurality of flexibility features along a proximal portion of the single piece of the partial cylinder and removing longitudinal portions of a section of a single piece of a partial cylinder includes making a plurality of cuts through a wall of the single piece of the partial cylinder. At least one of the plurality of cuts may be one of v-shaped, saw-shaped, and wave-shaped.

Methods may also include forming a texture of surface on an inward facing surface of at least one leg of the plurality of legs. The texture of surface may comprise one of teeth, spikes, serrations, and treads. The above method may further include forming an atraumatic tip at a distal end of the basket. Forming an atraumatic tip may include one of crimping and compressing the plurality of legs. Forming an atraumatic tip may also include filling the atraumatic tip with one of epoxy and brazing. Each leg of the plurality of legs may form an atraumatic tip at a distal end of the basket.

According to exemplary embodiments, a method of manufacturing also includes attaching retrieval material to at least two legs of the plurality of legs and attaching protection material to at least one of the basket and a proximal portion of the folded single piece. The protection material may be one of a sleeve, a tube, a sheath, a flat sheet, and a slab.

It is to be understood that both the foregoing general description and the following detailed description are exemplary and explanatory only, and are not restrictive of the invention as claimed.

BRIEF DESCRIPTION OF THE DRAWINGS

FIG. 13 illustrates still another embodiment of a stone retrieval device.

FIG. 14 illustrates a further embodiment of a stone retrieval device.

FIG. 15 is a cross-sectional view of the device of FIG. 14.

FIG. 16 is another cross-sectional view of the device of FIG. 14.

DETAILED DESCRIPTION

Exemplary embodiments of the present disclosure are illustrated in the accompanying drawings. Wherever possible, the same reference numbers will be used throughout the drawings to refer to the same or like parts.

Figure 1:
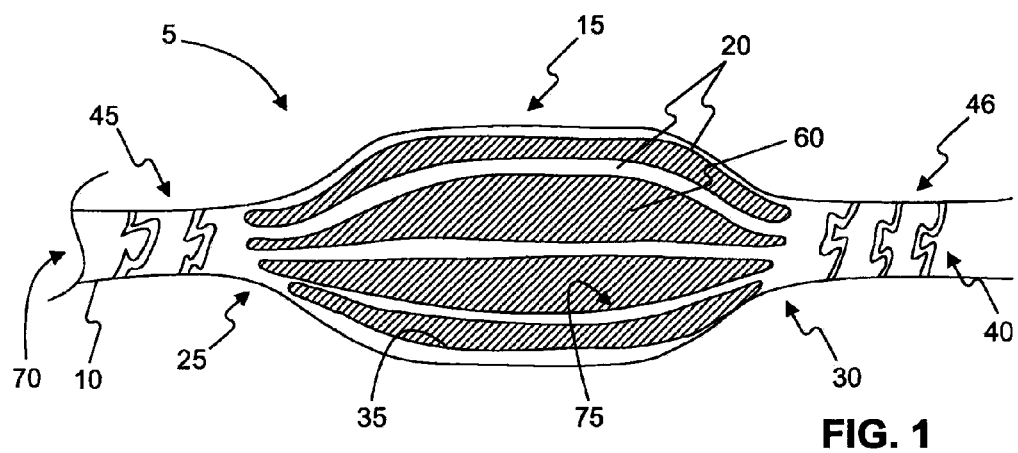
FIG. 1 illustrates a stone retrieval device according to an embodiment of the present disclosure.

FIG. 1 illustrates a stone retrieval device 5 according to an embodiment of the present disclosure. The device 5 includes an elongate member 10 and a basket 15 having a number of legs 20. The basket 15 may have a proximal end 25 and a distal end 30, and one or more of the legs 20 may have an inward facing surface 35 that is textured.

As shown in FIG. 1, the elongate member 10 may be formed from, for example, a rod, tube, cannula, stent, or other cylindrical piece of material, and may be hollow or solid. The elongate member 10 may also be formed from a portion of a cylindrical piece of material, or from a flat sheet of material. If formed from a flat sheet, the elongate member 10 may be formed into a cylindrical shape to form the basket 15. The elongate member 10 may be shaped to facilitate entry into and out of a sheath (not shown) and may include an open channel 70 therein.

The elongate member 10 may be formed from any biocompatible material known in the art. Such materials may include, but are not limited to, stainless steel (such as 300 and 400 series), cobalt chromium, nickel, titanium, nitinol, thermoforming plastic, polytetrafluoroethylene ("PTFE"), and expanded polytetrafluoroethylene ("ePTFE"). The elongate member 10 may also be a metal coated with a polymer.

The overall length and diameter of the elongate member 10 may vary depending on the application. For example, a relatively long elongate member 10 may be advantageous for retrieving stones or other calculi deep within the body of the patient. In addition, an elongate member 10 having a relatively small diameter may be advantageous for retrieving stones from restricted passageways within the human urinary tract.

As illustrated in FIG. 1, the elongate member may include a number of flexibility features 40. The flexibility features 40 may be cut into the elongate member 10 to increase the flexibility of either its proximal portion 45 or its distal portion 46. The flexibility features 40 may also increase the maneuverability of the device 5 while the device 5 is within the body of the patient.

As shown in FIG. 1, the flexibility features 40 may be positioned only along a portion of the proximal and distal portions 45, 46 of the elongate member 10 near to the basket 15. Although not shown, it is understood that the flexibility features could be positioned anywhere along the length of the proximal and distal portions 45, 46. The number and location of the flexibility features 40 may vary depending on the desired flexibility of the device 5. It is also understood that the distal portion 46 of the elongate member 10 may be shortened, or removed entirely, so that the basket 15 is at the distal-most end of the device. Thus, the distal end 30 of the basket 15 could be blunt, rounded, or tipless.

The flexibility features 40 may be formed by, for example, laser cutting, chemical etching, or mechanically slicing the same piece of material used to form the legs 20 of the basket 15. The cut for each flexibility feature 40 may extend partially or completely through the wall of the elongate member 10, and partially or completely around the entire width or circumference of the elongate member 10. Each flexibility feature may define a shape such as, for example, the dove-tail shape illustrated in FIG. 1. The shape may also interlock neighboring portions of the elongate member 10 that are partially or wholly separated by the cut. This shape may increase the flexibility of the device 5 and may improve the ability of device 5 to pass through complex, tortuous body structures.

The legs 20 of the basket 15 may be formed by, for example, laser cutting, chemical etching, die cutting, or mechanically slicing a single piece of material. The single piece of material may be the same piece of material as the elongate member 10. As a result, the width of the cuts may define the width and mechanical behavior of each of the basket legs 20, and the desired width may vary depending on the particular application. For example, it may be advantageous to have relatively narrow basket legs 20 when retrieving a relatively large stone from a body structure. Although FIG. 1 shows five legs around half of the circumference of the basket, it is understood that the basket 15 includes additional legs on the opposite side of the basket 15. In addition, other embodiments of the basket 15 may include any number of legs to facilitate the retrieval of a stone.

The length of the cuts may define the length and mechanical behavior of the basket legs 20, and the desired length may vary depending on the particular application. Each leg 20 may have the same length and width, or the length and width of each leg 20 may vary depending on the particular application. In addition, the spacing between the legs 20 may vary or be consistent.

The basket 15 may also include webbing, netting, or any other retrieval material 60 disposed between at least a portion of at least two of the basket legs 20. The retrieval material 60 may be polyvinylethylene ("PVE"), polyvinyl alcohol ("PVA"), ePTFE, PTFE, foam, or any other polymer or composite known in the art. The retrieval material 60 may form a partial barrier between the legs 20 of the basket 15, and may extend partially or completely along the length of the legs 20 between which it is disposed. The retrieval material 60 may allow, for example, fluid or other material to pass through while prohibiting, for example, stones from escaping the basket. The retrieval material 60 may be attached to the legs 20 through welding, grafting, tying, or any other attachment method known in the art. As will be described in greater detail later, the legs 20 of the basket 15 may be coated with a sheet of protection material 75 to protect the legs 20 during processes such as, for example, laser lithotripsy. It is understood that the configuration, material, and other characteristics of the basket 15 described herein permit it to assume a contracted, collapsed state for delivery to a treatment site in, for example, a sheath, and an expanded state for use at the treatment site.

FIGS. 2-5 and 13-16 illustrate stone retrieval devices 50 according to various embodiments of the present disclosure. The device 50 includes a basket 150 and a proximal portion 450, comprised of portions of an elongate member 100, for connection to the remainder of the medical device. As illustrated by FIGS. 2-5 and 13-16, the device 50 may be formed from a portion of a single piece of cylindrical material. The portion may be, for example, one-half of a single piece of cannula, stent, or other hollow tube known in the art.

Figure 6:
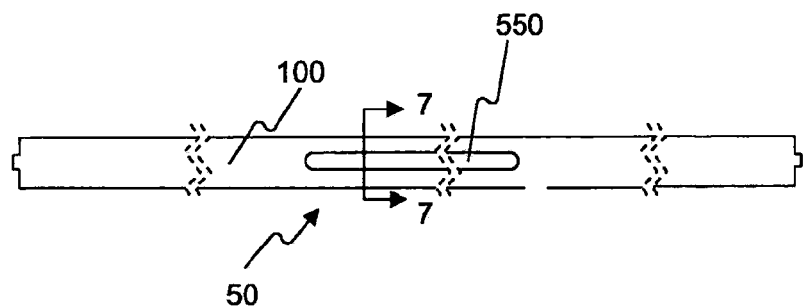
FIG. 6 illustrates an intermediate manufacturing step of a stone retrieval device according to another embodiment of the present disclosure.
Figure 7:
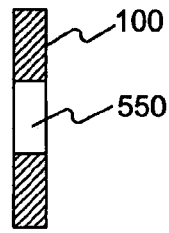
FIG. 7 is a cross-sectional view of the device of FIG. 6.
Figure 8:
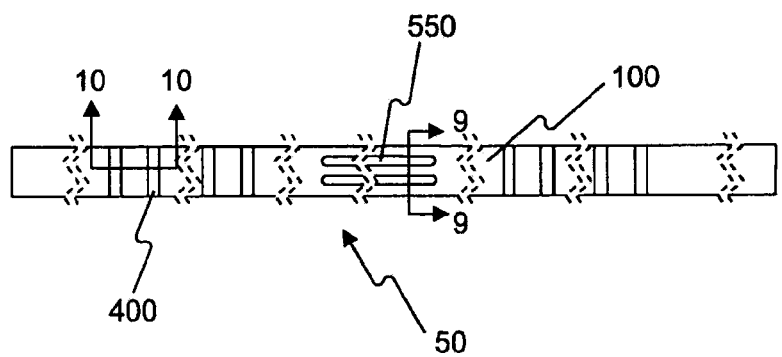
FIG. 8 illustrates an intermediate manufacturing step of a stone retrieval device according to still another embodiment of the present disclosure.
Figure 9:
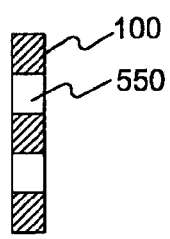
FIG. 9 is a cross-sectional view of the device of FIG. 8.
Figure 10:
FIG. 10 is a cut-away view of a portion of the device of FIG. 8.
Figure 11:
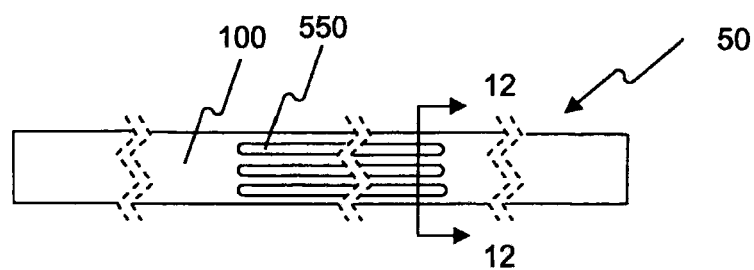
FIG. 11 illustrates an intermediate manufacturing step of a stone retrieval device according to a still further embodiment of the present disclosure.
Figure 12:
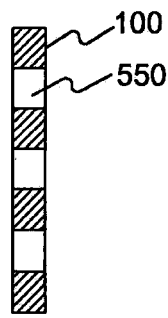
FIG. 12 is a cross-sectional view of the device of FIG. 11.

Alternatively, as shown in FIGS. 6-12 and 17-19, the device 50 may be formed from a portion of a single piece or sheet of flat material. For example, FIGS. 6 and 7 illustrate an embodiment of the present disclosure having a single cut 550. FIGS. 8-10 illustrate another embodiment having two cuts 550, and FIGS. 11 and 12 show yet another embodiment having three cuts 550. As shown in FIGS. 8 and 10, some embodiments of the device 50 may include flexibility features 400 similar to those described above with respect to FIG. 1.

To form the legs 200 of the basket 150, cuts 550 may be made through the wall of the elongate member 100. The number of cuts 550 may correspond to the number of legs 200 desired. The legs 200 may be of any length, width, or shape depending on the cuts 550 described above. For example, as shown in FIGS. 2, 6, 8, and 11, the cuts 550 may be substantially straight resulting in substantially straight legs 200. The cuts 550 are further illustrated in FIGS. 13-15.

Figure 3:
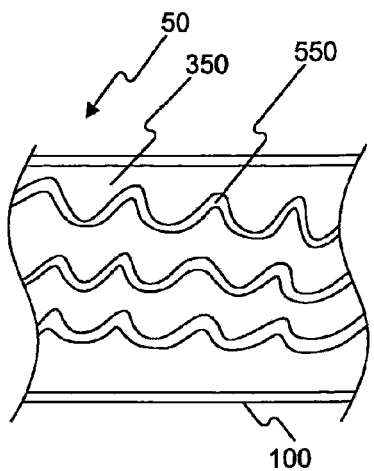
FIG. 3 illustrates a cut portion of a stone retrieval device according to a still further embodiment of the present disclosure.

The cuts 550 may also be, for example, wave-shaped as shown in FIG. 3, v-shaped (not shown), saw-shaped (also not shown), or any other shape to achieve desirable characteristics of legs 200. These cuts 550 may result in legs 200 having improved stone retrieval characteristics. As previously discussed, it is understood that the legs 200 may all have a similar size and shape, or can have different sizes and shapes.

Figure 2:
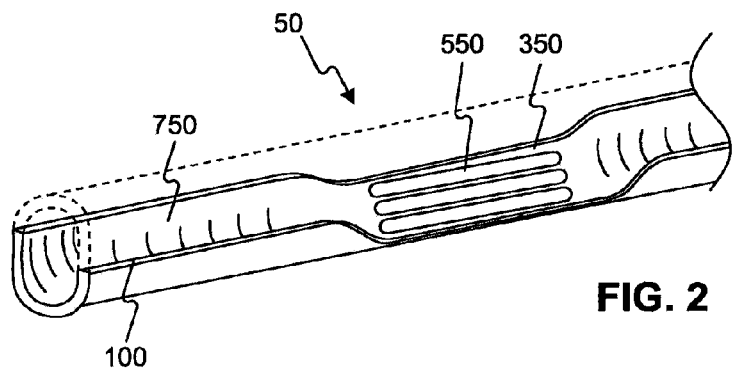
FIG. 2 illustrates an intermediate manufacturing step of a stone retrieval device according to another embodiment of the present disclosure.

FIG. 2 shows the inward facing surface 350 of each leg 200. Inward facing surface 350 may be textured to improve the stone retrieval capabilities of the device 50, and may include, for example, teeth, spikes, treads, serrations, or other structures known in the art. The texture of the inward facing surface 350 may provide multi-point contact with the stone and may be pointed away from sensitive tissue within the body structure so as not to cause trauma thereto.

Figure 4:
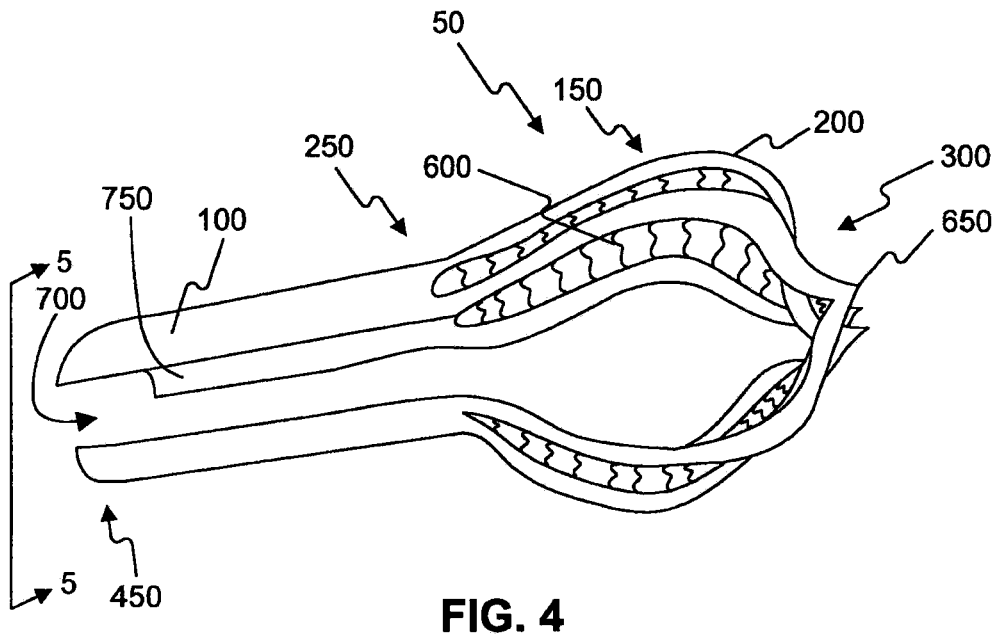
FIG. 4 illustrates the device of FIG. 2 folded to form the retrieval device.
Figure 17:
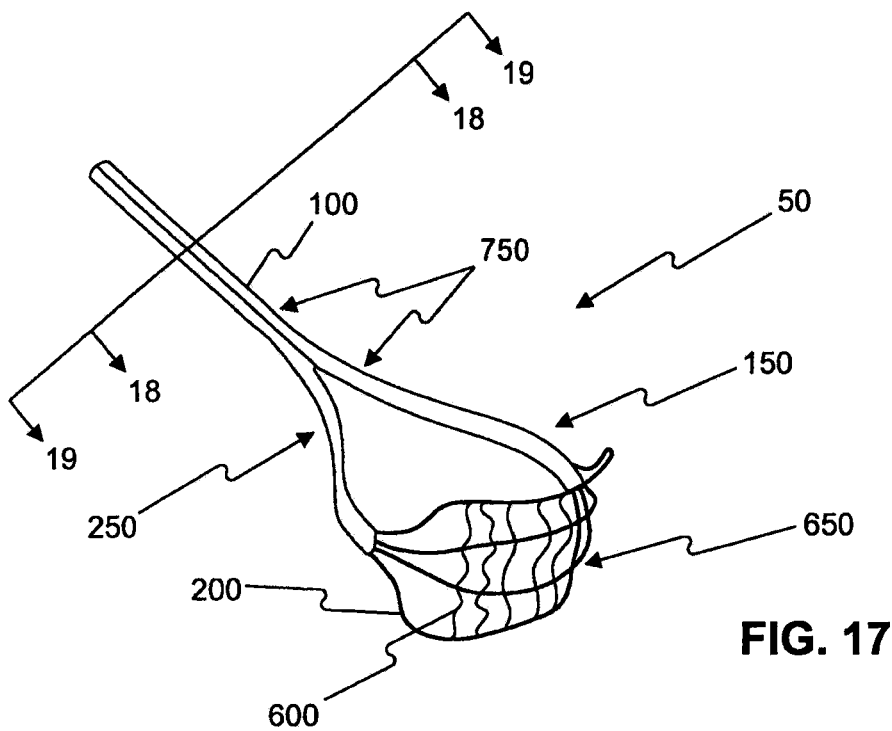
FIG. 17 illustrates an additional view of a stone retrieval device according to another embodiment of the present disclosure.

As illustrated in FIGS. 4 and 17, the elongate member 100 may be folded along the section into which the cuts 550 are made, and a basket tip 650 may be formed at the fold. The basket tip 650 may be, for example, blunt, rounded, or any other shape, and may be atraumatic so as not to cause damage to the body structure into which the device 50 is inserted. It is understood that each leg 200 may form a basket tip 650 as the member 100 is folded. The basket tip 650 may be formed by crimping or compressing at least a section of the legs 200 by any means known in the art, and may be filled or mounded with epoxy or brazing.

Retrieval material 600 may be attached to the legs 200 to assist in the retrieval of a stone. As in the FIG. 1 embodiment, the retrieval material 600 shown in at least FIG. 4 may protect the legs 200 during stone reduction processes such as, for example, laser lithotripsy. In addition, similar materials may be used for the legs 200, retrieval material 600, elongate member 100, basket 150 and other components of the FIG. 4 device 50 as described above with respect to FIG. 1.

As shown in FIG. 4, the retrieval material 600 may be attached to a portion of each neighboring leg 200. Alternatively, the retrieval material may only be attached to some of the legs 200 of the basket 150. It is understood that the retrieval material 600 may only be attached to a partial length of the legs 200 beginning at the distal end 300 of the basket 150. As shown for example in FIG. 17, the retrieval material 600 may extend between neighboring legs 200 and connect the neighboring legs 200 to each other at a distalmost end of the basket 150.

Figure 18:
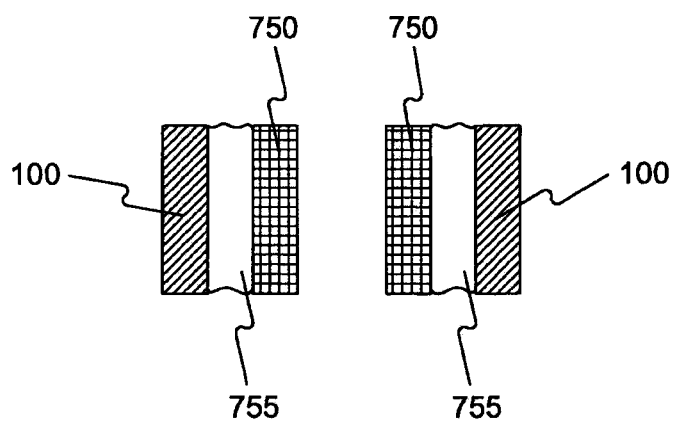
FIG. 18 is a cross-sectional view of one embodiment of the device of FIG. 17.
Figure 19:
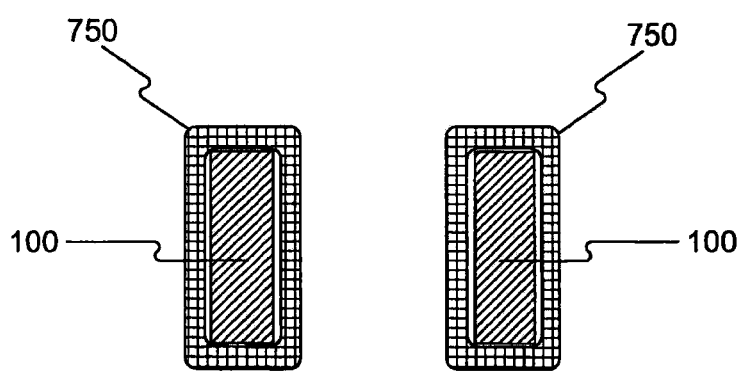
FIG. 19 is a cross-sectional view of another embodiment of the device of FIG. 17.

As illustrated in FIGS. 17-19, protection material 750 may also be attached to a portion of the proximal end 250 of the basket 150 and/or a portion of the elongate member 100. The protection material 750 may be any material capable of protecting the surfaces to which it is attached from procedures such as, for example, laser lithotripsy or other stone reduction procedures. Such materials include, but are not limited to, rubber, plastic, PTFE, ePTFE, PVA, polyurethane, or other like materials or composites. As illustrated in FIGS. 18 and 19, the protection material 750 may be, for example, a sleeve, tube, sheath, flat sheet, slab, or any other shape or structure known in the art. As illustrated in FIG. 18, the protection material 750 may be attached to the elongate member 100, or other parts of the device 50, with an adhesive 755 or other conventional attachment material or process known in the art. Alternatively, as shown in FIG. 19, the protection material 750 may fit snuggly over a portion of the device 50, eliminating the need for adhesive 755.

Once folded, the two halves of the elongate member 100 may oppose each other and may be connected to each other through soldering, welding, or other connection methods known in the art. As illustrated in FIG. 4, the two halves may form an open channel 700. The channel may provide a passage through which fluid may be injected into the body of the patient. The open channel 700 may be formed regardless of whether the two halves are physically connected, and that the channel 700 may also provide a passage through which another medical device such as, for example, a laser fiber, may pass.

Figure 5:
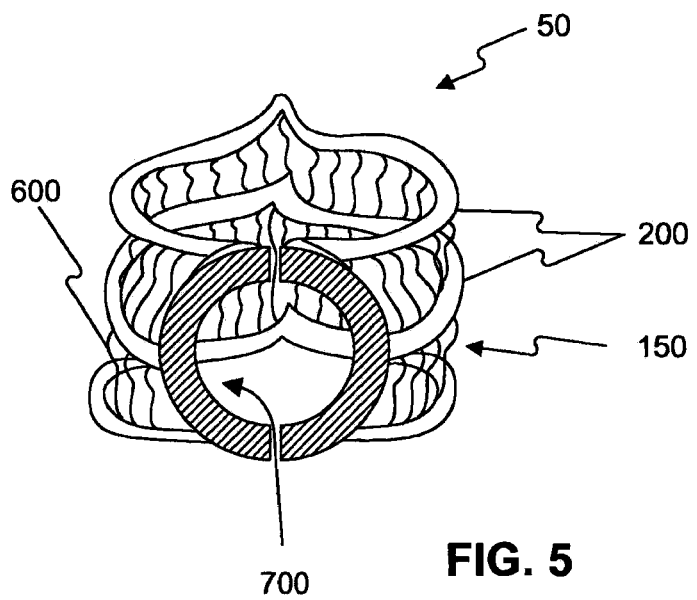
FIG. 5 is an end view of the device of FIG. 4.

FIG. 5 further illustrates open channel 700 and shows an embodiment in which the legs 200 are not connected at their distal end. It is understood that in this embodiment, the legs 200 may form two or more open loops without a distal tip. It is further understood that the loops may be rounded, layered, or otherwise shaped and spaced to assist in the capture and retrieval of a stone. Alternatively, the legs 200 may be crimped or pinched to form a tip 650 as shown in FIGS. 4 and 5. The tips 650 may be soldered, welded, or otherwise connected together to form a closed basket Referring again to FIG. 4, the two halves of the elongate member 100 may also be soldered, welded, or otherwise connected to a sheath, shaft, tube, mandrel, or other actuating member (not shown). In embodiments such as those shown in FIGS. 6-12 where the elongate member 100 is formed from a flat sheet of material, two ends of the elongate member 100 may be shaped according to the outside or inside diameter of the actuating member to facilitate connection thereto.

The actuating member may be hollow or solid, and may fit inside of, or over top of the two halves of the elongate member 100. If the actuating member is hollow, it may provide a channel that is operatively connected to, and in fluid communication with, the open channel 700 of the two halves of the elongate member 100. Thus, the channel of the actuating member may also provide a passage through which another medical device or injected fluid may pass.

The actuating member may be, for example, cylindrical, or any other shape facilitating the insertion and use of the device 50 within the human body. Moreover, the actuating member may be small enough to fit within a sheath, cannula, or lumen (not shown), and it may be advantageous to use the smallest possible actuating member depending on the condition of the patient and the location of the stone to be retrieved.

The legs 200 may be cold worked or heat processed to form a shape in memory. Thus, in an embodiment where an actuating member is used in conjunction with a sheath to deliver the device 50, the shape of the legs 200 may be fully formed once the sheath is retracted and the basket 150 is allowed to fully expand. Alternatively, the shape may be partially formed when the sheath is partially retracted. The resulting basket 150 may be any shape useful in capturing and/or retrieving a stone, and may be sized so as to be capable of capturing a stone in the range of approximately 4 mm to approximately 10 mm along its largest dimension.

At least some aspects of the present disclosure may be used, for example, to retrieve stones, calculi, or other material from any location within the body, such as, for example, in the urinary tract of the patient. The device 5, 50 may be inserted through the urethra of the patient, or alternatively, the device 5, 50 may be inserted percutaneously.

Although not shown, the stone targeted for retrieval may be a kidney stone, a struvite, a uric acid stone, a cystine stone, or other solid deposit commonly removed from a body structure or passageway within the body. Such stones may contain various combinations of chemicals including, but not limited to, calcium, oxalate, and phosphate. The stone may be of any size, and could have a length or diameter of approximately 1 mm to 12 mm. It is understood that these lengths and diameters are merely exemplary and that aspects of the present disclosure may assist in the retrieval of stones larger or smaller than those discussed herein. It is further understood that stones may be of any shape, and could be, for example, flat, round, smooth, or jagged. It is still further understood that the device 5, 50 may retrieve stones that are both impacted and free floating.

The retrieval device 5, 50 may be advanced to a treatment site within the body over a guidewire passing through all or a part of the open channel 70, 700. The device may also be advanced through an access sheath, stent, or other access or dilatation device known in the art. In addition, the device 5, 50 may be used in conjunction with an endoscope (not shown), or other type of intracorporeal scope known in the art. The endoscope may advance through the body over a guidewire to the treatment site. Alternatively, the endoscope may be independently fed to the treatment site without the use of a guidewire. Once the treatment site has been reached, the devices may be fed through an access port of the endoscope to gain access to the stone.

Relative motion between one or both of an actuating member (not shown) and a sheath (not shown) may move the basket 15, 150 into and out of the sheath and enable the basket 15, 150 to open and close. Thus, the stone may be captured within the open basket 15, 150 and retrieved by removing the device 5, 50 from the body of the patient.

The device 5, 50 may also assist in immobilizing a stone during stone reduction processes. For example, the basket 15, 150 may be positioned distal a stone so as to present a backstop and prevent particles of the stone from migrating or escaping from the treatment site during or after a laser fiber or other device acts to break up the stone. During such a procedure, the laser fiber may be fed to the stone through an open channel 70, 700 of the device 5, 50. Alternatively, the laser fiber may be fed through an access port of an endoscope, external to the device 5, 50, while the device 5, 50 is disposed within the same or a different endoscope. The laser fiber may be activated and otherwise controlled by the user while it is within the body of the patient, and a proximal end of the fiber may connect to a power source (not shown). Device 5, 50 may also act as a sweeping device to sweep out of the body, stones and stone particles obtained from a reduction process.

Other embodiments of the invention will be apparent to those skilled in the art from consideration of the specification and practice of the invention disclosed herein. For example, the device 5, 50 may include a handle operatively attached to an actuating member. In addition, the basket tips 65 may each be connected together, and the elongate member 10 may be formed from a piece of material having a square or rectangular cross-section. It is intended that the specification and examples be considered as exemplary only, with a true scope and spirit of the invention being indicated by the following claims.

What is claimed is:

1. A medical device, comprising:
an elongate member extending along a longitudinal axis;
a basket having a distal end and a plurality of legs, wherein each of the plurality of legs includes a loop extending between a first end of the elongate member and a second end of the elongate member that opposes the first end so as to form a basket tip at the distal end of the basket, and wherein the plurality of legs and the elongate member are a one single piece member;
retrieval material connecting together the loops and extending an entire length of each of the loops from the first end of the elongate member to the second end of the elongate member so as to prevent the basket tip of each leg from expanding outwardly relative to another basket tip along at least one axis perpendicular to the longitudinal axis; and
a plurality of flexibility features positioned along at least one of the first and second ends of the elongate member, wherein each of the plurality of flexibility features is discrete from each of the remaining flexibility features and from the plurality of legs.

2. The medical device of claim 1, wherein the loops are spaced apart from each other when the basket is in an expanded configuration.

3. The medical device of claim 1, wherein the retrieval material includes one of a webbing and a netting.

4. The medical device of claim 1, wherein the plurality of legs includes at least three legs, wherein a first end of each of the at least three legs is connected to the first end of the elongate member, and a second end of each of the at least three legs is connected to the second end of the elongate member.

5. The medical device of claim 1, wherein a first partial cylinder includes the first end of the elongate member, and a second partial cylinder includes the second end of the elongate member.

6. A medical device, comprising:
an elongate member extending along a longitudinal axis;
a basket having a distal end and a plurality of legs, wherein each of the plurality of legs includes a loop extending between a first half-portion of the elongate member and a second half-portion of the elongate member so as to form a basket tip at the distal end of the basket, wherein the elongate member and the plurality of legs are a one single piece member, and wherein the basket comprises retrieval material so as to restrict movement of the basket tip of a first loop relative to the basket tip of a second loop;
wherein each of the loops includes a first end and a second end, wherein each of the first ends of the loops is formed on the first half-portion of the elongate member, and each of the second ends of the loops is formed on the second half-portion of the elongate member; and
wherein the retrieval material connects the loops and extends along an entire length of each of the loops from the first half-portion of the elongate member to the second half-portion of the elongate member.

7. The medical device of claim 6, wherein the loops are spaced apart from each other when the basket is in an expanded configuration.

8. The medical device of claim 6, wherein the first half-portion is a first partial cylinder, and the second half-portion is a second partial cylinder.

9. The medical device of claim 8, wherein the first partial cylinder and the second partial cylinder are connected to form a lumen therethrough.

10. The medical device of claim 6, wherein the loops extend from the elongate member substantially parallel to each other.

11. The medical device of claim 6, wherein the plurality of legs includes at least three legs, wherein a first end of each of the at least three legs is connected to the first half-portion of the elongate member, and a second end of each of the at least three legs is connected to the second half-portion of the elongate member.

12. The medical device of claim 6, wherein the retrieval material includes one of a webbing and a netting.

13. A medical device, comprising:
an elongate member extending along a longitudinal axis and including a first half-portion and a second half-portion, wherein the first half-portion is positioned adjacent to the second half-portion to define a lumen of the elongate member; a basket having a distal end and a plurality of legs, wherein each of the plurality of legs includes a first end connected to the first half-portion of the elongate member and a second end connected to the second half-portion of the elongate member so as to form a basket tip at the distal end of the basket, wherein the basket comprises retrieval material so as to prevent the basket tip of each leg from expanding outwardly relative to another basket tip along at least one axis perpendicular to the longitudinal axis, wherein the elongate member and the plurality of legs are a one single piece member; and
the retrieval material connecting the plurality of legs and extending an entire length of each of the legs from the first end to the second end of each leg.

14. The medical device of claim 13, wherein the plurality of legs are spaced apart from each other when the basket is in an expanded configuration.

15. The medical device of claim 13, wherein each of the plurality of legs includes a loop extending from the first end of the leg to the second end of the leg.

16. The medical device of claim 13, wherein the first half-portion is a first partial cylinder, and the second half-portion is a second partial cylinder.

17. The medical device of claim 13, wherein the retrieval material includes one of a webbing and a netting.

18. The medical device of claim 13, wherein the plurality of legs includes at least three legs.

* * * * *